US012478719B2

(12) United States Patent
Forsland et al.

(10) Patent No.: US 12,478,719 B2
(45) Date of Patent: Nov. 25, 2025

(54) EMPTYING A BLOOD CIRCUIT AFTER EXTRACORPOREAL BLOOD TREATMENT

(71) Applicant: Gambro Lundia AB, Lund (SE)

(72) Inventors: Karl Henrik Forsland, Genarp (SE); Gunilla Andersson, Harlösa (SE)

(73) Assignee: Gambro Lundia AB, Lund (SE)

(*) Notice: Subject to any disclaimer, the term of this patent is extended or adjusted under 35 U.S.C. 154(b) by 724 days.

(21) Appl. No.: 17/609,218

(22) PCT Filed: Apr. 8, 2020

(86) PCT No.: PCT/EP2020/059979
§ 371 (c)(1),
(2) Date: Nov. 5, 2021

(87) PCT Pub. No.: WO2020/233895
PCT Pub. Date: Nov. 26, 2020

(65) Prior Publication Data
US 2022/0211928 A1 Jul. 7, 2022

(30) Foreign Application Priority Data
May 23, 2019 (SE) .................................. 1950610-4

(51) Int. Cl.
*A61M 1/36* (2006.01)
*A61M 1/14* (2006.01)
*A61M 1/16* (2006.01)

(52) U.S. Cl.
CPC ........... *A61M 1/365* (2014.02); *A61M 1/152* (2022.05); *A61M 1/15632* (2022.05);
(Continued)

(58) Field of Classification Search
None
See application file for complete search history.

(56) References Cited

U.S. PATENT DOCUMENTS 4,770,769 A * 9/1988 Schael ................ A61M 1/1639 210/257.2
5,591,344 A * 1/1997 Kenley .............. A61M 1/1682 210/764
(Continued)

FOREIGN PATENT DOCUMENTS

EP 3476414 A1 5/2019

*Primary Examiner* — Rebecca E Eisenberg
*Assistant Examiner* — Katherine-Ph Minh Pham
(74) *Attorney, Agent, or Firm* — K&L Gates LLP

(57) ABSTRACT

A blood treatment apparatus (1) defines first and second flow circuits (C1, C2) separated by a dialyzer (20). The second flow circuit (C2) comprises return and withdrawal lines (24', 24") for connection to a vascular system of a subject during a treatment session. After the treatment session, a control system causes an operator to connect the second flow circuit (C2) to a first port (32) of a container (30), the apparatus (1) to perform a rinseback procedure, the operator to disconnect the return line (24') from the vascular system and re-arrange the second flow circuit (C2) to define a closed loop, and the apparatus (1) to draw residual liquid from the closed loop into the first flow circuit (C1) through a dialyzer membrane (21). To facilitate drainage of the residual fluid with a conventional line set, the second flow circuit (C2) is connected to a second port (33) of the container (30) to include the container (30) in the closed loop, or the return and withdrawal lines (24', 24") are connected in fluid communication with the first port of the container (30) through a three-way manifold coupling unit.

28 Claims, 7 Drawing Sheets

(52) U.S. Cl.
CPC ...... *A61M 1/1694* (2013.01); *A61M 1/36222* (2022.05); *A61M 1/36225* (2022.05); *A61M 1/362265* (2022.05); *A61M 1/3627* (2013.01); *A61M 1/3646* (2014.02); *A61M 1/3653* (2013.01); *A61M 1/154* (2022.05); *A61M 1/36224* (2022.05); *A61M 1/362262* (2022.05)

(56) References Cited

U.S. PATENT DOCUMENTS

| | | | | |
|---|---|---|---|---|
| 7,588,684 | B2 | 9/2009 | Brugger et al. | |
| 2003/0010717 | A1* | 1/2003 | Brugger | A61M 1/3646 210/252 |
| 2003/0100857 | A1* | 5/2003 | Pedrazzi | A61M 1/3644 604/4.01 |
| 2005/0131332 | A1* | 6/2005 | Kelly | A61M 1/362265 604/4.01 |
| 2010/0087772 | A1* | 4/2010 | Gronau | A61M 1/3646 604/6.11 |
| 2010/0168640 | A1 | 7/2010 | Kopperschmidt et al. | |
| 2012/0000547 | A1 | 1/2012 | Gronau et al. | |
| 2013/0025697 | A1 | 1/2013 | Blasek et al. | |
| 2016/0058935 | A1* | 3/2016 | Hundertmark | F16K 31/60 137/15.05 |
| 2017/0209638 | A1 | 7/2017 | Hacker et al. | |
| 2017/0296733 | A1* | 10/2017 | Riemenschneider | A61M 1/3626 |
| 2018/0256807 | A1 | 9/2018 | Brugger et al. | |
| 2018/0280604 | A1* | 10/2018 | Hobro | A61M 1/16 |
| 2019/0083692 | A1* | 3/2019 | Plahey | A61M 1/28 |

* cited by examiner

EMPTYING A BLOOD CIRCUIT AFTER EXTRACORPOREAL BLOOD TREATMENT

PRIORITY CLAIM

The present application is a National Phase of International Application No. PCT/EP2020/059979, filed Aug. 4, 2020, which claims priority to SE Application No. 1950610-4, filed May 23, 2019. The entire contents of each application are incorporated herein by reference and relied upon.

TECHNICAL FIELD

The present invention relates to operating an extracorporeal blood treatment apparatus, e.g. a dialysis machine, and in particular to a technique of emptying a blood circuit subsequent to blood treatment.

BACKGROUND ART

Extracorporeal blood treatment, such as hemodialysis, is performed by an apparatus that is configured to supply one or more fluids for use in the treatment. Equipment that is exposed to blood during treatment is typically replaced after each treatment. Such disposable equipment may include a dialyzer and a line set with tubing for defining an extracorporeal blood circuit for conducting blood from a patient, through the dialyzer and back to the patient. During a treatment session, the extracorporeal circuit is connected to the patient at a withdrawal end and a return end, respectively, and a blood pump of the apparatus is operated to pump the patient's blood through the blood circuit while one or more pressure sensors of the apparatus are connected in fluid communication with the line set to monitor the pressure in the blood circuit.

Conventionally, at the end of a blood treatment session, the blood pump is stopped and a so-called rinseback procedure is initiated. Attending staff disconnects the withdrawal end from the patient and connects it to a bag containing a physiological saline solution, whereupon the blood pump is operated so that the saline solution pushes most of the blood present in the blood circuit back into the patient. Then, when the blood pump is stopped, attending staff may disconnect the return end from the patient and place the disposable equipment in a special container for contaminated waste. To reduce weight, the staff may first carry the dialyzer, the line set and the bag to a nearby sink or container for draining of remaining fluid. Alternatively, the attending staff may start a draining procedure on the apparatus, whereby the apparatus operates the blood pump to pump remaining fluid through the return connector into the nearby sink or container.

This conventional procedure involves a considerable risk of blood and blood-containing saline solution being spilled on the apparatus and its surroundings.

The prior art comprises US2003/0100857 which proposes to procedure for draining the blood circuit via the dialyzer by use of a specialized line set. In contrast to conventional line sets, the specialized line set includes a dedicated branch tube which is terminated by a connector that is specifically configured for interconnection with a connector on the return end of the line set. After rinseback and while the withdrawal end is connected to a flexible bag of saline solution, the caretaker connects the connector on the branch tube to the connector on the return end so as to form a closed loop. The apparatus then operates the blood pump to circulate the remaining fluid in the closed loop and controls one or more of its dialysis fluid pumps to create a pressure gradient over the membrane of the dialyzer, so as to drive the remaining liquid through the membrane into the apparatus for safe disposal. To benefit from the technique proposed in US2003/0100857, dialysis clinics are required to acquire and keep in stock the specialized line set. This is undesirable from a logistic point of view and increases operating cost and internal handling and storage at the dialysis clinics. Further, it is currently believed that it may be difficult to ensure a sufficient drainage of the blood circuit by use of the proposed line set and the associated draining procedure.

SUMMARY

It is an objective of the invention to at least partly overcome one or more limitations of the prior art.

A further objective is to provide a technique that enables draining of the blood circuit after completed blood treatment by use of a conventional line set.

Another objective is to facilitate or improve automated draining of the blood circuit.

One or more of these objectives, as well as further objectives that may appear from the description below, are at least partly achieved by a control system, a blood treatment apparatus, a method and a computer readable medium in accordance with first and second inventive concepts as defined by the independent claims, embodiments thereof being defined by dependent claims.

A first aspect is a control system for a blood treatment apparatus. The blood treatment apparatus comprises a fluid supply unit and is configured for installation of a dialyzer and a line set to define a first flow circuit for conducting a fluid provided by the fluid supply unit through the dialyzer and back to the fluid supply unit, and to define a second flow circuit which is separated from the first flow circuit by a semi-permeable membrane of the dialyzer and comprises return and withdrawal lines for connection to a vascular system of a subject during a blood treatment session. The control system is configured to, subsequent to a termination of the blood treatment session: instruct an operator to connect the second flow circuit to a first port of a container that holds a human-compatible fluid; operate the blood treatment apparatus to push remaining blood in the second flow circuit into the vascular system of the subject through the return line while admitting the human-compatible fluid from the container into the second flow circuit; instruct the operator to disconnect the return line from the vascular system of the subject and re-arrange the second flow circuit to define a closed loop; and operate, in a draining phase, the blood treatment apparatus to draw residual liquid from the closed loop into the first flow circuit through the semi-permeable membrane of the dialyzer.

In accordance with the first inventive concept, the control system is further configured to instruct the operator to re-arrange the second flow circuit by connecting the second flow circuit to a second port of the container so that the container is included in the closed loop.

Generally, the first inventive concept enables the second flow circuit and the container to be substantially drained of residual fluid in the draining phase by a combination of automated control and operator instructions. According to the first inventive concept, the second flow circuit is connected in fluid communication with two separate ports of the container in the draining phase. Such use of a container that has more than one port enables the closed loop to be formed by a simple and conventional line set. For example, the ports on the container may be configured for connection, directly or indirectly, to any two suitable existing connectors of such a conventional line set, e.g. terminal connectors on the ends of the withdrawal and return lines. Further, by arranging the container within the closed loop, the residual fluid is circulated through the container in the draining phase, which serves to counteract the formation of obstructions to the flow within the container or at the ports. Thereby, the first inventive concept also improves the ability of the blood treatment apparatus to perform an automated draining of the second flow circuit.

In some embodiments of the control system of the first inventive concept, in the closed loop, the withdrawal line is connected in fluid communication with the first port of the container and the return line is connected in fluid communication with the second port of the container.

In some embodiments of the control system of the first inventive concept, in the closed loop, terminating connectors on the withdrawal and return lines are connected, directly or indirectly, to the first and second ports, respectively, of the container.

In some embodiments of the control system of the first inventive concept, the control system is further configured to, in the draining phase, operate the blood treatment apparatus to circulate the residual liquid in the closed loop, and thus through the container.

In accordance with the second inventive concept, the control system further is configured to instruct the operator to re-arrange the second flow circuit by connecting the return and withdrawal lines in fluid communication with the first port of the container through a three-way manifold coupling unit.

Generally, the second inventive concept enables the closed loop to be formed by a simple and conventional line set since the three-way manifold coupling unit, when connected to the first port of the container, provides two ports for connection, directly or indirectly, to any two existing connectors of a conventional line set, e.g. terminal connectors on the ends of the withdrawal and return lines.

In some embodiments of the control system of the second inventive concept, in the closed loop, a first port of the three-way manifold coupling unit is connected in fluid communication with the first port of the container, a second port of the three-way manifold coupling unit is connected in fluid communication with the withdrawal line, and a third port of the three-way manifold coupling unit is connected in fluid communication with the return line.

In some embodiments of the control system of the second inventive concept, the control system is further configured to, in the draining phase, operate the blood treatment apparatus to circulate the residual liquid in the closed loop.

In the following, further embodiments of the control system are defined and are applicable to both of the first and second inventive concepts. These embodiments provide at least some of the technical effects and advantages described in the foregoing, as well as additional technical effects and advantages as readily understood by the skilled person in view of the following detailed description.

In some embodiments, the control system is further configured to, in the draining phase, operate a clamp of the blood treatment apparatus to selectively open a branch line, which is included in the line set and is arranged in fluid communication with the second flow circuit, so as to ventilate the closed loop.

In some embodiments, the control system is configured to, during the draining phase, operate the clamp to keep the branch line open and only intermittently close the branch line.

In some embodiments, the control system is configured to, in the draining phase, operate the clamp to repeatedly close the branch line, e.g. for 0.1-10 seconds, and preferably for 0.4-5 seconds.

In some embodiments, the control system is configured to, when terminating the draining phase, operate the clamp to close the branch line, operate the blood treatment apparatus to generate a sub-atmospheric pressure in the thus-closed branch line, and operate the clamp to open the branch line to release the sub-atmospheric pressure.

In some embodiments, one of the return and withdrawal lines is arranged in the clamp during the blood treatment session, and the control system is further configured to, before the draining phase, instruct the operator to remove said one of the return and withdrawal lines from the clamp and install the branch line in the clamp.

In some embodiments, the branch line is branched from the withdrawal line.

In some embodiments, the control system is further configured to, before the draining phase, instruct the operator to disconnect the branch line from a sensor port of the blood treatment apparatus.

In some embodiment, the return line is arranged in the clamp and the withdrawal line is arranged in a further clamp of the blood treatment apparatus during the blood treatment session, the branch line is branched from the withdrawal line downstream of the further clamp, and the control system is further configured to, before the draining phase, instruct the operator to remove the return line from the clamp, install the branch line in the clamp, and instruct the operator to disconnect the branch line from a sensor port of the blood treatment apparatus, wherein the control system is further configured to, before instructing the operator to disconnect the branch line, close the further clamp and operate the blood treatment apparatus to generate a sub-atmospheric pressure in the withdrawal line downstream of the further clamp and in the branch line.

In some embodiments, the fluid supply unit defines a drain flow path which extends from an inlet port for connection to the first flow circuit to a drain pump, wherein the drain flow path comprises a set of sensors and an inlet valve intermediate the inlet port and the set of sensors, wherein the fluid supply unit further defines a supply flow path, which comprises an outlet valve and extends from a supply pump to an outlet port for connection to the first flow circuit, and wherein the control system is further configured to, in the draining phase: close the outlet and inlet valves; open a valve located in a connecting line, which extends between a first location in the drain flow path intermediate the inlet port and the inlet valve and a second location in the drain flow path intermediate the drain pump and the set of sensors; and operate the drain pump to draw the residual liquid from the closed loop into the first flow circuit through the semi-permeable membrane of the dialyzer and from the first flow circuit into the drain flow path via the inlet port.

In some embodiments, the connecting line extends from a degassing device in the drain flow path, and wherein the control system is further configured to, during the blood treatment session, open the valve in the connecting line to expel gases from the degassing device through the connecting line.

In some embodiments, the control system is further configured to, in the draining phase: open a bypass valve in a bypass line, which extends between a third location in the drain flow path intermediate the inlet valve and the second location, and a fourth location in the supply flow path intermediate the supply pump and the outlet valve, so as to establish fluid communication between the inlet port and a pressure sensor in the supply flow path; and control the drain pump based on a pressure signal from the pressure sensor.

A second aspect is a blood treatment machine comprising a fluid supply unit configured to supply a fluid to a first flow circuit, a pump operable to engage with a second flow circuit, and the control system in accordance with the first or second inventive concept or any embodiment thereof.

A third aspect is a method of operating a blood treatment apparatus that comprises a fluid supply unit and is configured for installation of a dialyzer and a line set to define a first flow circuit for conducting a fluid provided by the fluid supply unit through the dialyzer and back to the fluid supply unit, and to define a second flow circuit which is separated from the first flow circuit by a semi-permeable membrane of the dialyzer and comprises return and withdrawal lines for connection to a vascular system of a subject during a blood treatment session. The method comprises, subsequent to a rinseback procedure and while the withdrawal line is connected to a first port of a container and when the return line has been disconnected from the vascular system of the subject: causing a re-arrangement of the second flow circuit to define a closed loop; and operating, in a draining phase, the blood treatment apparatus to draw residual liquid from the closed loop into the first flow circuit through the semi-permeable membrane of the dialyzer.

In the method of the first inventive concept, the re-arrangement comprises connecting the second flow circuit to a second port of the container so that the container is included in the closed loop.

In some embodiments of the method of the first inventive concept, the re-arrangement comprises connecting the withdrawal line in fluid communication with the first port of the container and connecting the return line in fluid communication with the second port of the container.

In some embodiments of the method of the first inventive concept, the re-arrangement comprises connecting terminating connectors on the withdrawal and return lines, directly or indirectly, to the first and second ports, respectively, of the container.

In some embodiments, the method of the first inventive concept further comprises: operating, in the draining phase, the blood treatment apparatus to circulate the residual liquid in the closed loop, and thus through the container.

In the method of the second inventive concept, the re-arrangement comprises connecting the return and withdrawal lines in fluid communication with the first port of the container through a three-way manifold coupling unit.

In some embodiments of the method of the second inventive concept, the re-arrangement results in a first port of the three-way manifold coupling unit being connected in fluid communication with the first port of the container, a second port of the three-way manifold coupling unit being connected in fluid communication with the withdrawal line, and a third port of the three-way manifold coupling unit being connected in fluid communication with the return line.

In some embodiments, the method of the second inventive concept further comprises, in the draining phase, operating the blood treatment apparatus to circulate the residual liquid in the closed loop.

In the following, further embodiments of the method are defined and are applicable to both of the first and second inventive concepts.

In some embodiments, the method further comprises, in the draining phase, operating a clamp to selectively open a branch line, which is included in the line set and is arranged in fluid communication with the second flow circuit, so as to ventilate the closed loop.

In some embodiments, the method comprises, during the draining phase, operating the clamp to keep the branch line open and only intermittently closing the branch line.

In some embodiments, the method further comprises, in the draining phase, operating the clamp to repeatedly close the branch line, e.g. for 0.1-10 seconds, and preferably for 0.4-5 seconds.

In some embodiments, the method further comprises, when terminating the draining phase: operating the clamp to close the branch line; operating the blood treatment apparatus to generate a sub-atmospheric pressure in the thus-closed branch line; operating the clamp to open the branch line to release the sub-atmospheric pressure.

In some embodiments of the method, one of the return and withdrawal lines is arranged in the clamp during the blood treatment session, and the method further comprises, before the draining phase, removing said one of the return and withdrawal lines from the clamp and installing the branch line in the clamp.

In some embodiment of the method, the branch line is branched from the withdrawal line.

In some embodiments, the method further comprises, before the draining phase, disconnecting the branch line from a sensor port of the blood treatment apparatus.

In some embodiments, the return line is arranged in the clamp and the withdrawal line is arranged in a further clamp of the blood treatment apparatus during the blood treatment session, and the branch line is branched from the withdrawal line downstream of the further clamp, wherein the method further comprises, before the draining phase, removing the return line from the clamp, installing the branch line in the clamp, and disconnecting the branch line from a sensor port of the blood treatment apparatus, and wherein the method further comprises, before said disconnecting the branch line, closing the further clamp and operating the blood treatment apparatus to generate a sub-atmospheric pressure in the withdrawal line downstream of the further clamp and in the branch line.

In some embodiments of the method, the fluid supply unit is configured to define a drain flow path, which extends from an inlet port for connection to the first flow circuit to a drain pump and which comprises a set of sensors and an inlet valve intermediate the inlet port and the set of sensors, and a supply flow path, which comprises an outlet valve and extends from a supply pump to an outlet port for connection to the first flow circuit, and the method further comprises, in the draining phase: closing the outlet and inlet valves; opening a valve located in a connecting line, which extends between a first location in the drain flow path intermediate the inlet port and inlet valve and a second location in the drain flow path intermediate the drain pump and the set of sensors; and operating the drain pump to draw the residual liquid from the closed loop into the first flow circuit through the semi-permeable membrane of the dialyzer and from the first flow circuit into the drain flow path via the inlet port.

In some embodiments of the method, the connecting line extends from a degassing device in the drain flow path, and the method further comprises, during the blood treatment session, opening the valve in the connecting line to expel gases from the degassing device through the connecting line.

In some embodiments, the method further comprises, in the draining phase: opening a bypass valve in a bypass line, which extends between a third location in the drain flow path intermediate the inlet valve and the second location and a fourth location in the supply flow path intermediate the supply pump and the outlet valve, so as to establish fluid communication between the inlet port and a pressure sensor in the supply flow path; and controlling the drain pump based on a pressure signal from the pressure sensor.

A fourth aspect is a computer-readable medium comprising computer instructions which, when executed by a processor, cause the processor to perform the method in accordance with the first or second inventive concept or any embodiment thereof.

Still other objectives, features, embodiments, aspects and advantages of the present invention may appear from the following detailed description, from the attached claims as well as from the drawings.

BRIEF DESCRIPTION OF THE DRAWINGS

Embodiments of the invention will now be described in more detail with reference to the accompanying drawings.

DETAILED DESCRIPTION OF EXAMPLE EMBODIMENTS

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

In the following, embodiments of the invention will be exemplified with reference to an apparatus configured for treatment of renal failure, denoted "dialysis machine" below.

Figure 1:
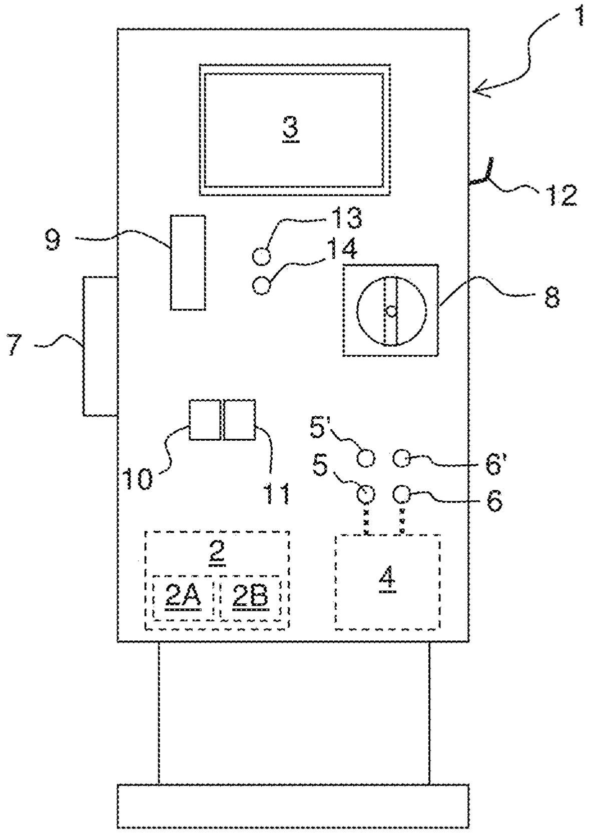
FIG. 1 is a schematic front view of a dialysis machine.

FIG. 1 shows an example of such a dialysis machine 1, which is operable to perform a dialysis treatment when combined with a set of disposable products or "disposables" to be described below with reference to FIG. 2. The dialysis machine 1 in FIG. 1 is also known as "monitor" and defines a machine chassis that exposes holders for mounting the disposable(s) in operative engagement with components such as connectors, pumps, sensors, clamps, etc. The disposables are exposed to circulating blood and are typically for single-use, i.e. they are discarded after each treatment session.

In the illustrated example, a control system or controller 2 in the machine 1 is configured to synchronize and control the operation of the components of the machine 1, e.g. by electric control signals. The operation of the control system 2 may be at least partly controlled by software instructions that are supplied on a computer-readable medium for execution by a processor 2A in conjunction with a memory 2B in the control system 2. A display unit 3 is operable to provide information and instructions for an operator, such as a nurse, a physician or a patient. The machine 1 may also enable the operator to enter data into the machine, e.g. via mechanical buttons (not shown) or virtual buttons on a touch panel, e.g. in the display unit 3. A fluid supply unit 4 is configured to supply one or more suitable fluids during operation of the machine 1. Such fluids may include one of more of a treatment fluid (dialysis fluid) for use during blood treatment, a disinfectant for use in disinfection of the machine between treatments, a saline solution, and purified water. The fluids may be supplied from replaceable containers attached to the machine 1 or may be generated on demand by the machine 1 or another apparatus in fluid communication with the machine 1. In the illustrated example, the machine comprises machine ports 5, 6, 5', 6' in fluid connection to the supply unit 4. The machine ports 5, 6 are input and output ports, respectively, for a human-compatible fluid such as a treatment fluid, saline solution or water, whereas the machine ports 5', 6' are input and output ports, respectively, for a disinfectant. The machine 1 further comprises a holder 7 for a dialyzer (20 in FIG. 2), a machine-controlled peristaltic pump ("blood pump") 8 for engagement with a withdrawal line (24" in FIG. 2), and a holder 9 for a drip chamber (25 in FIG. 2), and two machine-controlled clamps 10, 11. Further, a holder 12 is provided for a container (30 in FIGS. 4A-4B). The machine 1 also comprises sensor ports 13, 14 in fluid communication with pressure sensors (not shown) within the machine 1. The skilled person realizes that the machine 1 may comprise further components that are not shown in FIG. 1A, e.g. a blood detector, an injection system for anticoagulant, etc.

Figure 2:
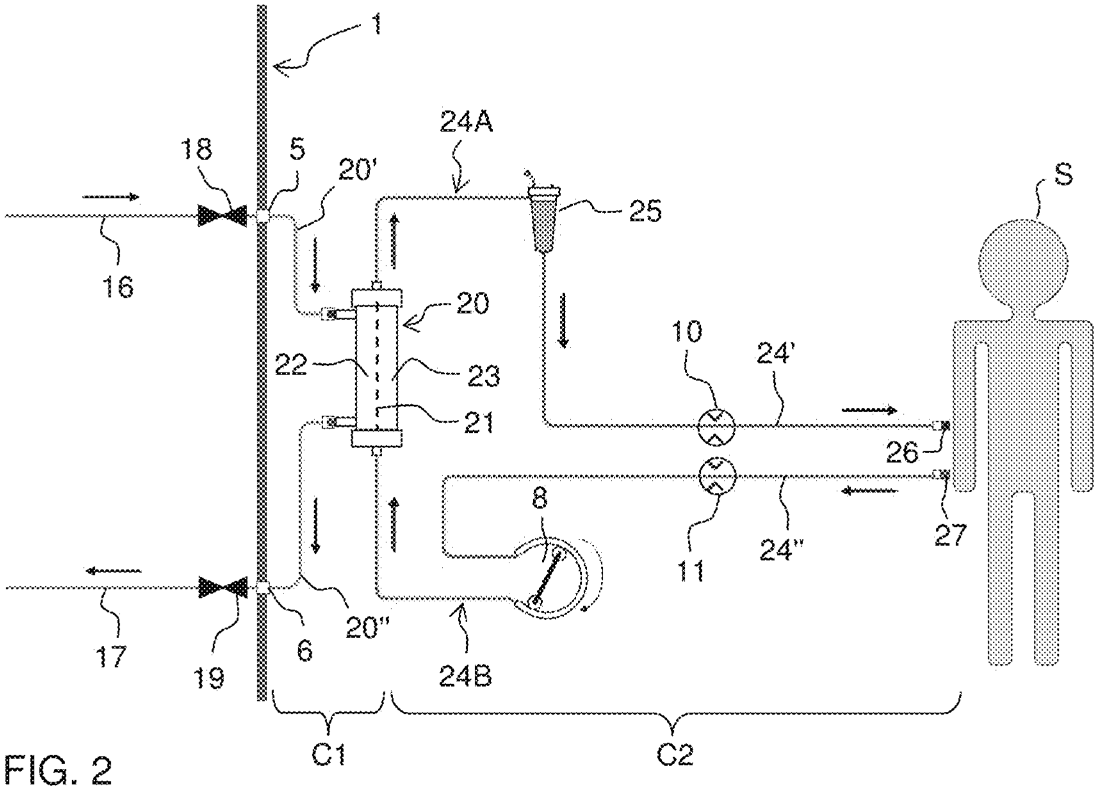
FIG. 2 is a schematic diagram of a dialysis machine connected and operated for blood treatment.

FIG. 2 illustrates a dialysis machine 1, e.g. as shown in FIG. 1, which is connected to a set of disposables and operated for hemodialysis treatment of a subject S, in this example a human patient. The set of disposables includes a dialyzer 20, which is a blood filtration unit configured for fluid connection to a line set (below) and for fluid connection to the machine ports 5, 6. A semi-permeable membrane 21 ("dialyzer membrane") is arranged inside the housing of the dialyzer 20 to separate a first chamber ("dialysis fluid side compartment") 22 from a second chamber ("blood side compartment") 23. The first and second chambers 22, 23 are configured to be perfused by blood and dialysis fluid, respectively, during blood treatment. The set of disposables further includes fluid-conducting devices in the form of first and second line arrangements 24A, 24B, which are collectively known as a "line set" in the art. The first line arrangement 24A comprises a drip chamber 25 and flexible tubing that defines a flow path extending from a first end with a dialyzer connector to a second end having a terminal connector 26. In the following, the tubing 24' that extends to the terminal connector 26 is denoted "return line". The second line arrangement 24B comprises flexible tubing that defines a flow path from a first end with a terminal connector 27 to a second end with a dialyzer connector. In the following, the tubing 24" that extends to the terminal connector 27 is denoted "withdrawal line". The line arrangements 24A, 24B and the dialyzer 20 may be provided as separate components that are interconnected before use, or they may be delivered as a preassembled unit. Although not shown in FIG. 2, each of the line arrangements 24A, 24B may include further components, such as one or more manual clamps, one or more branch lines for dedicated use such as connection to a pressure sensor (cf. sensor ports 13, 14 in FIG. 1), infusion of anticoagulant, replacement fluid, etc.

As understood from FIG. 2, the disposables have been mounted to the machine 1 by attaching the dialyzer 20 to holder 7 (FIG. 1) and the drip chamber 25 to holder 9 (FIG. 1), by arranging the withdrawal line 24" for engagement with pump 8 and clamp 11 ("withdrawal clamp"), and by arranging the return line 24' for engagement with clamp 10 ("return clamp"). The set of disposables is connected for fluid communication with the dialysis machine 1 so as to define a first flow circuit C1 ("dialysis fluid circuit") for dialysis fluid supplied by the dialysis machine 1 and a second flow circuit C2 ("extracorporeal blood circuit") which is connected to the vascular system of the subject S. Specifically, the dialyzer 20 is connected by a supply line 20' and a drain line 20" to establish fluid communication between the first chamber 22 and the ports 5, 6, thereby forming the first flow circuit C1. Further, the dialyzer 20 is connected for establishing fluid communication between the second chamber 23 and the line arrangements 24A, 24B, thereby forming the second flow circuit C2. During blood treatment, the terminal connectors 26, 27 are connected to a blood vessel access of the subject S. As is well-known in the art, the blood vessel access (also known as "vascular access") may be a fistula, graft or catheter, and the terminal connectors 26, 27 may be connected to the blood vessel access by any conventional device, including needles or catheters.

FIG. 2 also illustrates fluid lines 16, 17 that extend inside the machine 1 from the fluid supply unit 4 (FIG. 1) to the ports 5, 6, via machine-operated outlet and inlet valves 18, 19 for selectively opening and closing the ports 5, 6. In the following, filled and non-filled valve symbols indicate that a valve is open and closed, respectively.

In FIG. 2, the machine 1 is operated by the control system 2 (FIG. 1) to open the valves 18, 19 and establish a flow of dialysis fluid through the first chamber 22 of the dialyzer 20, as indicated by arrows. The machine 1 is also operated by the control system 2 to open clamps 10, 11 and run pump 8 so that blood is drawn from the vascular system of the subject S along line arrangement 24B, pushed through the second chamber 23 of the dialyzer 20 and back to the vascular subject S along line arrangement 24A, as indicated by arrows, while the blood is being subjected to dialysis treatment in the dialyzer 20. Dialysis treatment as such is well-known to the person skilled in the art and will not be described in detail herein.

When dialysis treatment is completed, it is common practice to return all or most of the blood remaining in the second flow circuit C2 to the vascular system of the subject S. This process is known as "rinseback" or "reinfusion" and involves pushing at least a portion of the remaining blood into the subject S while introducing a rinseback fluid into the second flow circuit C2. After rinseback, the second flow circuit C2 contains a residual fluid in the form of a mixture of rinseback fluid and blood. Embodiments of the invention aim at facilitating disposal of the residual fluid.

Figure 3A:
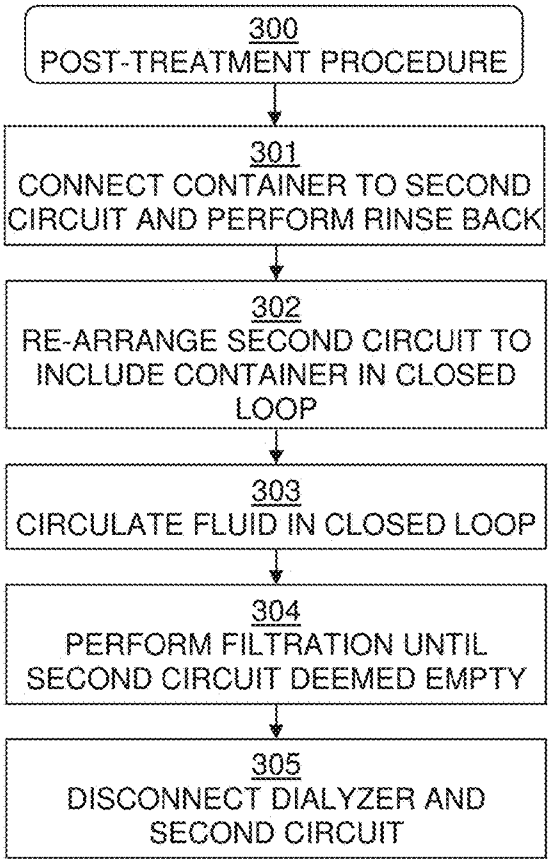
FIGS. 3A-3B are flow charts of methods of operating a dialysis machine in accordance with a first and a second inventive concept, respectively.

In the following, an embodiment of a first inventive concept will be described with reference to the flow chart in FIG. 3A in combination with system diagrams in FIGS. 4A-4B, which illustrate a dialysis machine 1 when arranged and operated for rinseback and drainage of residual fluid, respectively. The flow chart in FIG. 3A represents a post-treatment procedure 300 that includes rinseback, a draining phase and removal of disposables. Each of the steps 301-305 of the method 300 may be controlled by the control system 2 of the dialysis machine 1. To the extent that a step involves a manual operation, the control system 2 may generate and present corresponding instructions for the operator, e.g. on the display 3, and may also require the operator to confirm when the manual operation has been completed, e.g. by pressing or touching a button on the machine 1. However, it also conceivable that one or more of the steps are independently performed by the operator based on written instructions, e.g. from an operations manual or work guide, without involvement of the control system 2.

The procedure 300 is initiated after termination of the dialysis treatment in FIG. 2. The dialysis treatment may be terminated by the machine 1 stopping the blood pump 8, closing the clamps 10, 11, and closing the valves 18, 19. In a rinseback step 301, the operator connects a container 30, which contains a human-compatible fluid ("rinseback fluid"), to the second flow circuit C2 and the machine 1 is operated to perform the above-mentioned rinseback. The rinseback fluid may be any fluid, which by its composition is compatible with the human body if administered to its circulatory system in relevant amounts, including but not limited to a saline solution, a treatment fluid, and water.

Figure 4A:
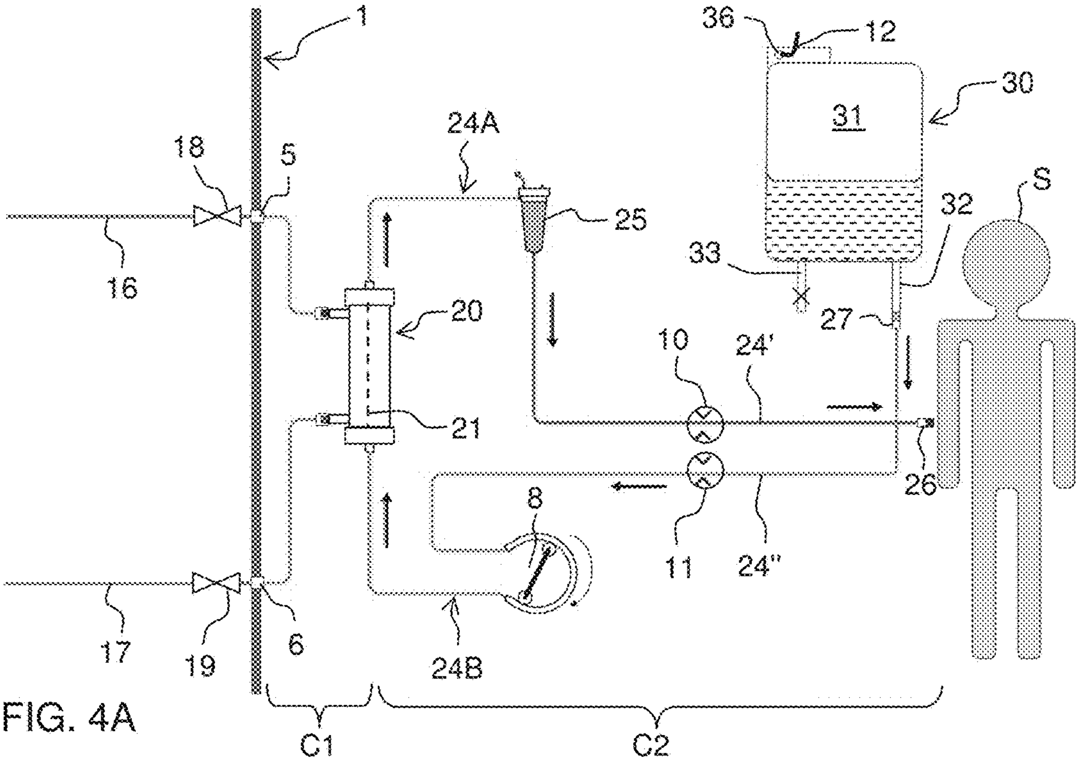
FIGS. 4A-4B are schematic diagrams of a dialysis machine connected and operated in accordance with the first inventive concept.

As shown in FIG. 4A, the rinseback fluid is held within an internal space 31 of the container 30, which comprises an outlet port 32 and an inlet port 33 in fluid communication with the internal space 31. The container 30 may be made of rigid or flexible material, preferably a transparent or translucent material that allows for ocular inspection of the contents in the container 30. In the illustrated example, the container 30 further defines a suspension hole 36.

In the example of FIG. 4A, step 301 involves instructing the operator to disconnect the terminal connector 27 from the vascular access of the subject S and connect the terminal connector 27 to the outlet port 32 of the container 30. The dialysis machine 1 then opens clamps 10, 11 and operates pump 8 to push the remaining in the second flow circuit C2 into the subject S while drawing rinseback fluid from the container 30 into the withdrawal line 24", as indicated by arrows in FIG. 4A, until all or a majority of the remaining blood in the second flow circuit C2 has been returned to the subject S. The machine 1 then stops pump 8 and closes clamps 10, 11. The rinseback may be terminated manually by the operator or automatically by the machine 1 based on input from a dedicated sensor (not shown).

In a re-arrangement step 302, which is performed after termination of the rinseback step 301, the operator is instructed to re-arrange the second flow circuit C2 to form a closed loop that includes the container 30. In the example of FIG. 4B, the closed loop is formed by connecting the terminal connector 26 on the return line 24' to the inlet port 33 of the container 30.

After step 302, the machine 1 enters a draining phase that includes a circulation step 303 and a filtration step 304.

Figure 4B:
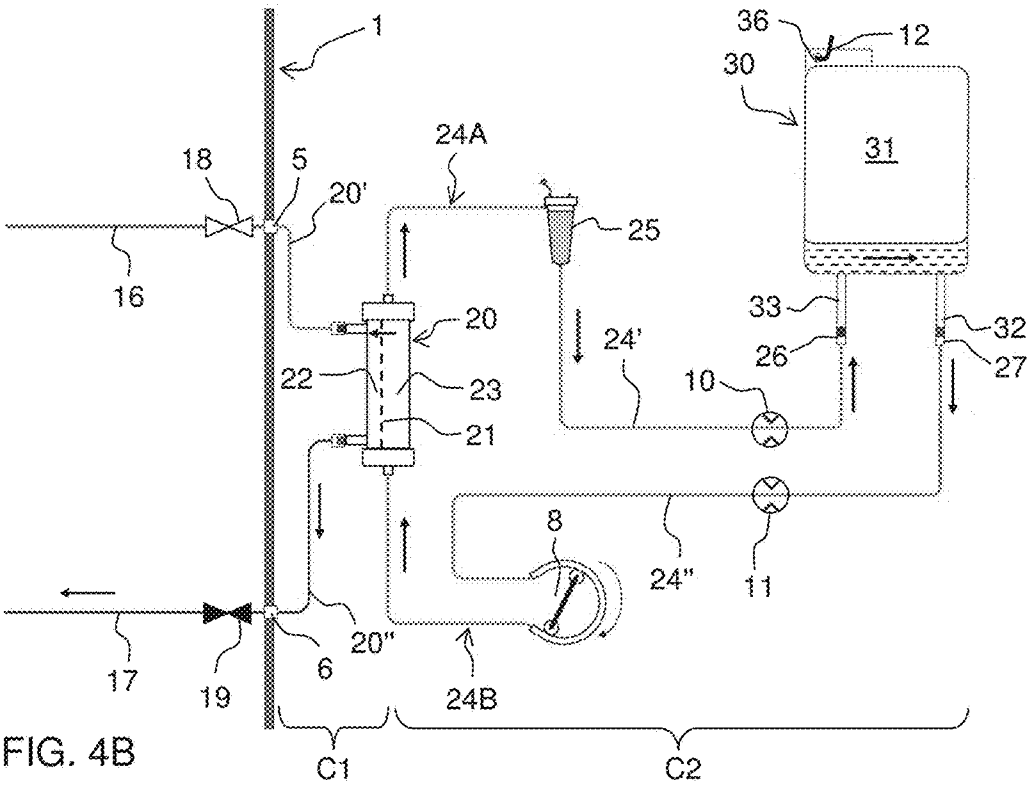

In the circulation step 303, the machine 1 is operated to open clamps 10, 11 and start pump 8 to circulate the residual fluid in (along) the closed loop, as indicated by arrows in FIG. 4B. The residual fluid is composed of remaining rinseback fluid in the container 30 and a mixture of rinseback fluid and blood residues in the line arrangements 24A, 24B and in the second chamber 23 of the dialyzer 20.

In the filtration step 304, the machine 1 is operated to draw residual fluid from the second flow circuit C2 into the first flow circuit C1 through the membrane 21, and from the first flow circuit C1 into the drain line 17 of the machine 1, as indicated by arrows in FIG. 4B. This process, denoted "filtration" herein, may be achieved by controlling the machine 1 to generate a lower pressure in the first chamber 22 compared to the second chamber 23. In the illustrated example, inlet valve 19 is opened, outlet valve 18 is closed and the fluid supply unit 4 is operated to generate suction on drain line 17, to thereby reduce the pressure in the first chamber 22 and draw residual fluid across the membrane 21. In an alternative, both valves 18, 19 are opened and the fluid supply unit 4 is operated to supply a fluid, e.g. a dialysis fluid, to the supply line 16 and to establish a higher flow rate in the drain line 17 than in the supply line 16. The filtration of step 304 may be at least partly concurrent with the circulation of step 303. It is conceivable that the machine 1 is operated to alternate between filtration and circulation. Steps 303 and 304 are terminated when the second flow circuit C2 is deemed to be sufficiently drained of residual fluid. Steps 303 and 304 may be terminated by the operator, e.g. by pressing a button on the machine, or automatically by the machine 1, e.g. based on dead-reckoning of the volume pumped into the patient by the pump 8 and/or based on input from a sensor, such as a pressure sensor in fluid communication with the closed loop (cf. P1, P2 in FIGS. 6A-6B) and/or a pressure sensor in the fluid supply unit (cf. P3 in FIGS. 9A-9B).

Finally, in step 305, clamps 10, 11 are opened and the operator is instructed to strip the machine 1 of the set of disposables by disconnecting the dialyzer 20, the line arrangements 24A, 24B and the container 30, preferably as a unit. The operator may then discard the set of disposables. Subsequently, the machine 1 may perform a conventional disinfection procedure, e.g. after instructing the operator to connect tubing 20', 20" to ports 5', 6' (FIG. 1).

The procedure 300 enables the closed loop, including the container 30, to be substantially drained of residual fluid during the draining phase. This reduces the weight of the set of disposables to be discarded and also reduces the risk that residual fluid is spilled on and around the machine 1. As understood from FIGS. 4A-4B, by enabling the second fluid circuit C2 to be connected to two separate ports 32, 33 on the container 30, the procedure 300 may be implemented by use of a simple and conventional line set and by use of a conventional dialysis machine 1. Further, it is currently believed that the circulation of residual fluid through the container 30 serves to facilitate draining of the closed loop. For example, the inflow of residual fluid through the inlet port 33 may serve to reduce the risk of the outlet port 32 becoming obstructed before the container 30 is completely drained. Such obstruction may occur, e.g., if the container is compliant (flexible) and gradually collapses as the amount of residual fluid in the container 30 diminishes.

By experimentation, the inventors have found that the draining of the closed loop may be facilitated if the closed loop is vented to the atmosphere during the filtration and/or between periods of filtration (step 304). Such venting will counteract formation of negative (sub-atmospheric) pressure in the closed loop by the filtration, and thereby ensure a sufficient pressure difference between the chambers 23, 22 as well as counteract flow resistance caused by negative pressure, e.g. a collapsing of the container 30 (if flexible). For automated draining, the venting is preferably machine-controlled.

An embodiment that enables such machine-controlled venting by use of a simple and conventional line set will now be described with reference to a flow chart in FIG. 5 in combination with system diagrams in FIGS. 6A-6B, which illustrate a dialysis machine 1 when arranged and operated for blood treatment and drainage of residual fluid, respectively. In the illustrated example, the line arrangement 24A includes a branch line 28 in fluid communication with the drip chamber 25 and extending to a connector for connection to sensor port 13, which is in fluid communication with a first pressure sensor P1 in the machine 1. The line arrangement 24B includes a branch line 29 in fluid communication with the withdrawal line 24" and extending to a connector for connection to sensor port 14, which is in fluid communication with a second pressure sensor P2 in the machine 1. As is well-known to the skilled person and shown in FIG. 6A, the branch lines 28, 29 are connected to the ports 13, 14 during blood treatment, thereby enabling the machine 1 to monitor pressure (aka "arterial pressure") on the withdrawal side of the second flow circuit C2 upstream of the pump 8, and pressure (aka "venous pressure") on the return side of the second flow circuit C2.

Figure 6A:
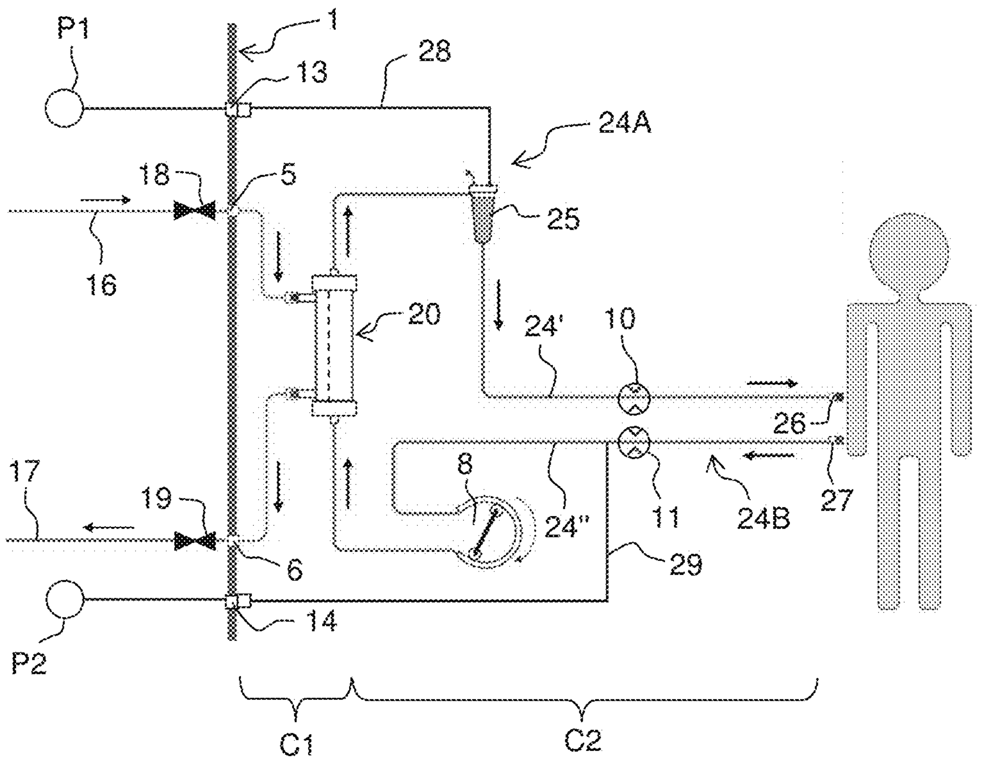
FIGS. 6A-6C are schematic diagrams of a dialysis machine connected and operated in accordance with the first inventive concept.
Figure 6B:
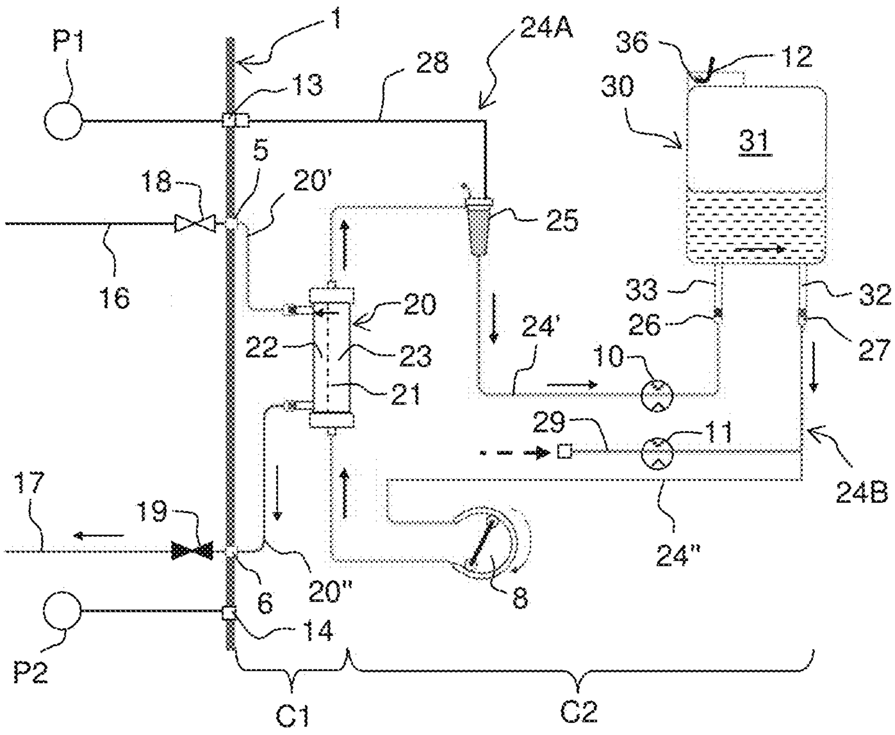

The procedure 500 is performed when the blood treatment in FIG. 6A has been terminated and includes an initial rinseback step 501, which may be identical to step 301, and a re-arrangement step 502, which may be identical to step 302 and results in connectors 26, 27 being connected to ports 33, 32 of container 30, as seen in FIG. 6B. After step 502, the operator is instructed to remove the withdrawal line 24" from the clamp 11, which is opened (step 503), disconnect branch line 29 from sensor port 14 so that the terminal end of branch line 29 is open to the environment (step 504), and install branch line 29 in clamp 11 so that clamp 11 is operable to selectively open and close branch line 29 (step 505). The procedure 500 then proceeds to the draining phase, by performing a circulation step 506 and a filtration step 507 in correspondence with steps 303 and 304 as described above, as well as a ventilation step 508, in which clamp 11 is opened to vent the closed loop, for reasons explained above.

The ventilation in step 508 may differ depending on implementation. In one embodiment, steps 506 and 507 are performed with open clamps 10, 11 to ensure proper filtration and circulation, as illustrated in FIG. 6B, in which a dashed arrow designates air that enters the opened branch line 29. However, the inventors have found that the draining of the closed loop may be facilitated, particularly at end of the draining phase when small amounts of residual fluid remain in the container 30, if clamp 11 is intermittently closed during circulation and/or filtration. In one example, the clamp 11 is closed during a fraction of the duration of the draining phase, e.g. less than 20%, 15%, 10% or 5%. Thus, the branch line is kept open during the draining phase except for one or more short time periods in which the branch line is closed. In fact, the inventors have found that draining may be improved by toggling the clamp 11, particularly towards the end of the draining phase. In such toggling, the clamp 11 is repeatedly (2 or more times) switched to close and then re-open the branch line 29. In one embodiment, the clamp 11 is intermittently closed for 0.1-10 seconds, and preferably 0.4-5 seconds, during the toggling. In step 509, when the second flow circuit C2 is deemed, by operator input or based on sensor data, to be sufficiently drained of residual fluid the clamps 10, 11 are closed. After a predefined wait time AT (step 510), the pump 8 is stopped and filtration is terminated (step 511). Optionally, the filtration may be stopped already at step 509 or step 510. By operating the pump 8 during the wait time ΔT, a negative pressure is established in branch line 29. This will reduce risk of residual fluid leaking out of the branch line 29 when the clamps 10, 11 are subsequently opened for disconnection of the disposables (cf. step 305). In an alternative, only clamp 10 is closed in step 509, and clamp 11 is subsequently closed in step 511. This may further reduce the risk of liquid leaking from the branch line 29 when disconnected after completed draining phase.

The procedure 500 may be implemented by use of a simple and conventional line set and by use of a conventional dialysis machine 1 and enables facilitated draining of the second flow circuit C2 by machine-controlled venting of the closed loop.

Figure 6C:
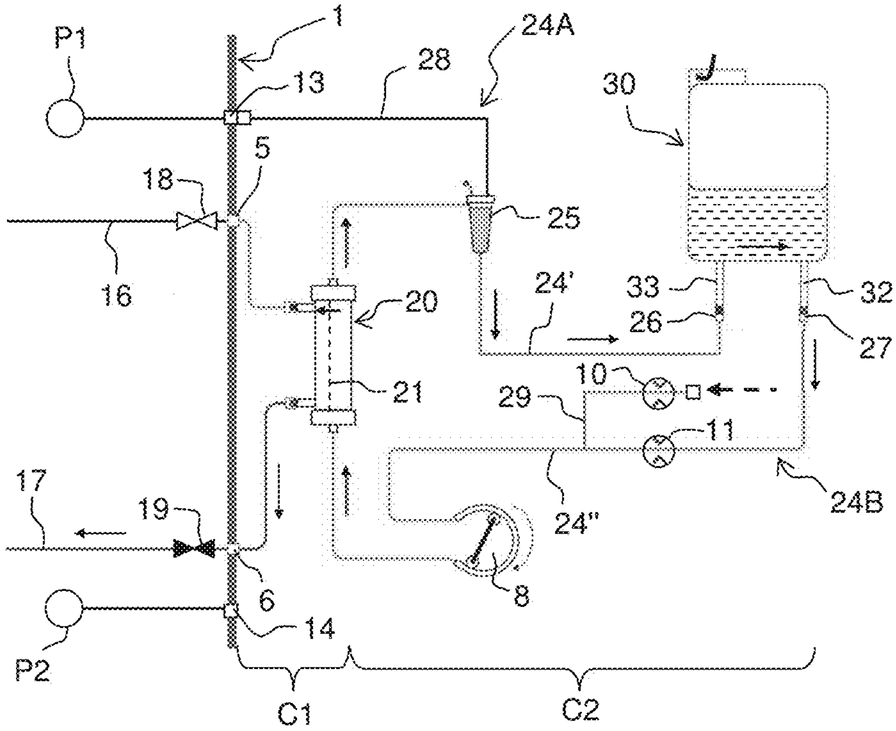

It is to be realized that corresponding effects may be achieved if steps 503, 505 are modified to instruct the operator to replace the return line 24' by the branch line 29 in clamp 10, resulting in the configuration shown in FIG. 6C. All other steps of the procedure 500 may be implemented as described with reference to FIG. 6B. However, to facilitate draining in step 508, clamp 10 is operated for ventilation/toggling. Further, only clamp 11 may be closed in step 509, whereas clamp 10 may be subsequently closed in step 511. The installation of the branch line 29 in clamp 10 enables a dedicated leakage prevention procedure to be performed between steps 502 and 504. In this procedure, the control system 2 closes clamp 11 and then operates pump 8 to generate negative pressure in the withdrawal line 24" downstream of the clamp 11 and in the branch line 29. The control system 2 may stop the blood pump 8 after a predefined time or when a predefined pressure is attained in the branch line 29, e.g. indicated by the pressure sensor P2. The negative pressure reduces the risk of blood leakage when the branch line 29 is disconnected from the sensor port 14 in step 504.

The installation of the branch line 29 in clamp 11 as shown in FIG. 6B, or in clamp 10 as shown in FIG. 6C, has the advantage of enabling the blood pump 8 to generate a negative pressure in the branch line 29 by steps 509-511.

In further alternatives, not shown, steps 503-505 are modified to instruct the operator to disconnect branch line 28 from sensor port 13 and install branch line 28 in either of clamps 10, 11.

The implementation of the procedure 500 may depend on the particular combination of dialysis machine and line set, e.g. which branch line 28, 29 is long enough to be arranged in which clamp 10, 11.

In all embodiments herein, the above-mentioned negative pressure may be generated by operation of the blood pump 8 and/or by performing filtration through the dialyzer membrane.

There may be situations when it is not possible or desirable to use a two-port container 30 as described hereinabove. Instead, a single-port container may be preferred. For example, a dialysis clinic may want to keep an existing supply chain of single-port containers, may want to avoid stock-keeping of different container types, etc. When using a single-port container, it is equally important to avoid the need for a specialized line set to perform machine-controlled draining of the blood circuit after completed blood treatment.

This objective may be achieved in accordance with a second inventive concept by use of a three-way manifold coupling unit, which defines three ports and an internal manifold that fluidly connects the ports. Such a coupling unit may also be denoted "T coupling" or "Y coupling" in the art. One port of the coupling unit is connected to the port of the single-port container to provide two ports for connection to the return and withdrawal lines of a line set. By such an arrangement, a closed loop may be formed by use of a conventional line set, where the container is fluidly connected to the closed loop by the coupling unit, but is located outside of the closed loop. Experiments show that the closed loop and the container may be substantially drained of residual fluid by performing the above-described filtration to draw the residual fluid into the dialysis machine through the dialyzer membrane.

Figure 3B:
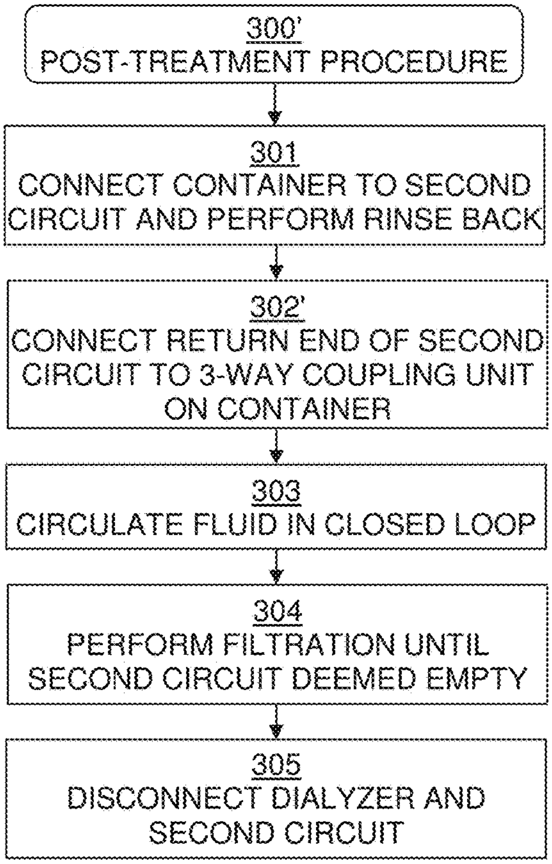
Figure 7:
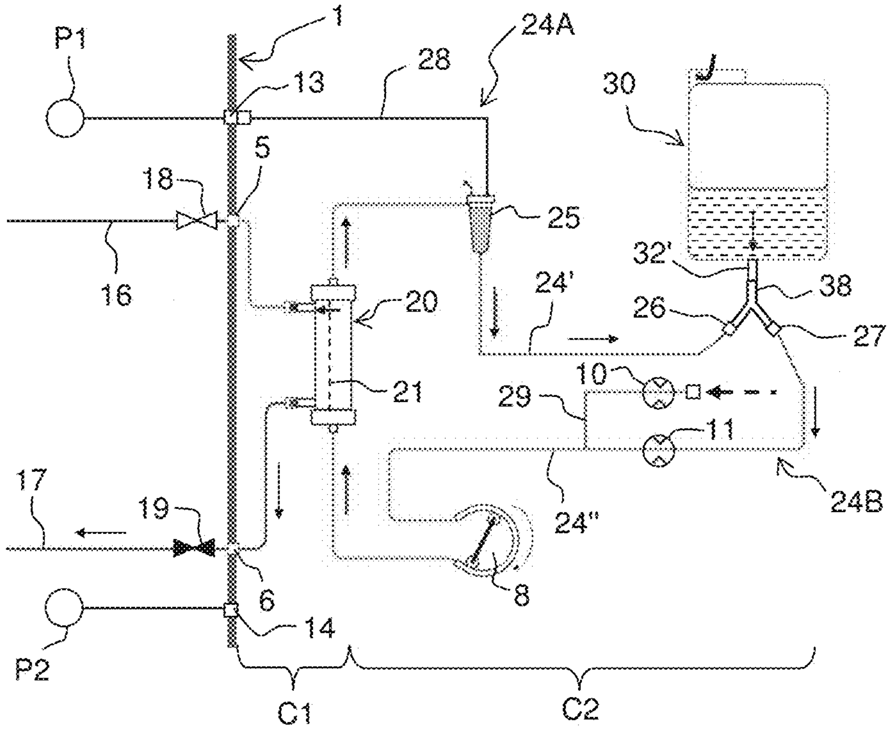
FIG. 7 is a schematic diagram of a dialysis machine connected and operated in accordance with the second inventive concept.

In the following, an embodiment of the second inventive concept will be described with reference to the flow chart in FIG. 3B in combination with the system diagram in FIG. 7, which includes a container 30 with a single port 32' and otherwise corresponds to FIG. 6C. The flow chart in FIG. 3B corresponds to FIG. 3A and represents a post-treatment procedure 300' that includes rinseback, a draining phase and removal of disposables. Unless otherwise stated, the description of FIG. 3A is equally applicable to FIG. 3B. The procedure 300' differs from the procedure 300 by the re-arrangement step 302', in which the operator is instructed to connect a first port of a 3-way manifold coupling unit 38 to the container port 32' and to connect the terminal connectors 26, 27 to second and third ports of the coupling unit 38. It is realized from FIG. 7 that the provision of the coupling unit 38 enables the use of a conventional line set and that steps 301, 303-305 may be performed as described for FIG. 3A. As indicated by an arrow in FIG. 7, fluid is drawn from the container 30 into the closed loop by the filtration (step 304). In a variant, the coupling unit 38 is connected to the container port 32' already in step 301, i.e. in preparation for the rinseback procedure. For example, step 301 may involve connecting the first port of the coupling unit 38 to the container port 32' and connecting the connector 27 on the withdrawal line 24" to the second port of the coupling unit 38, while ensuring that the third port of the coupling unit 38 is closed. The dialysis machine then performs rinseback. Then, in step 302, the operator may be instructed to form the closed loop by connecting the connector 26 on the return line 24' to the third port of the coupling 28.

Figure 5:
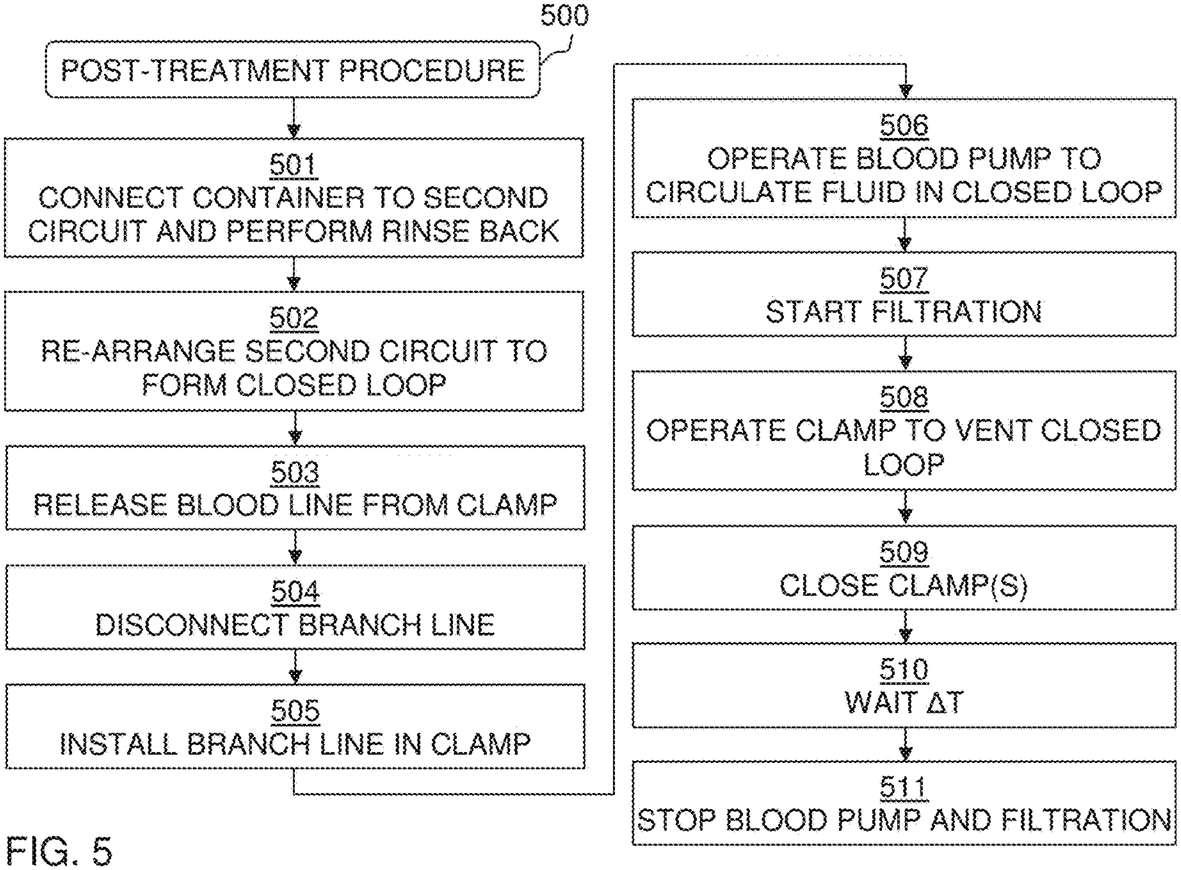
FIG. 5 is a flow chart of a method of operating a dialysis machine in accordance with the first or second inventive concepts.

The description of the procedure 500 in FIG. 5 is also applicable to the second inventive concept, given that step 502 is modified in correspondence with step 302'. As noted, the coupling unit 38 may optionally be connected to the container port 32' already in step 501. All embodiments described with reference to FIGS. 6A-6C are equally applicable to the second inventive concept.

Experiments conducted by the inventors indicate that the venting step 508, and in particular the toggling of the branch line during the venting step 508, results in a significant reduction in the time required for draining the second flow circuit C2 in accordance with the second inventive concept. The toggling will provide a motive force that actively pulls fluid from the container into the closed loop and thereby reduces the time required for draining the container 30.

As a non-limiting example, the first and second inventive concepts may be implemented to substantially drain the second fluid circuit C2 and the container 30 of residual fluid in 1-3 minutes, assuming that the total volume of residual fluid to be drained is less than approx. 0.5-0.8 L and that the dialyzer 20 has a high-flux or high-permeability membrane (having an ultrafiltration capacity of more than 20 mL/h/mmHg). As used herein, "substantially drain" may indicate that the total remaining amount of residual fluid after the draining phase is no more than 0.1 L, and preferably no more than 0.05 L.

By insightful reasoning, the inventors have found that it might be advantageous to avoid exposing sensitive components in the fluid supply unit 4 to the residual fluid, which may include blood residues. For example, exposing sensors to the residual fluid might lead to fouling that causes the machine 1 to malfunction. Thus, in one embodiment, a drain flow path within the fluid supply unit 4 is modified during filtration compared to blood treatment to avoid such exposure. Furthermore, the flow paths within the fluid supply unit 4 may be modified such that the output signal of a pressure sensor in the fluid supply unit 4 represents pressure in the first chamber 22 of the dialyzer 20, allowing the control system 2 to at least partly control the filtration based on the output signal.

Figure 9A:
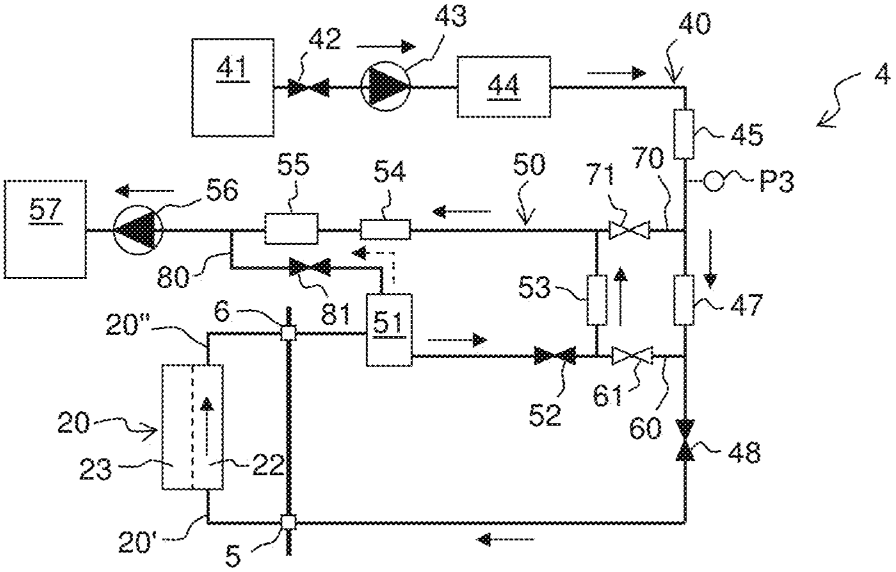
FIGS. 9A-9B are schematic diagrams of a fluid supply unit operated in accordance with FIG. 8.
Figure 9B:
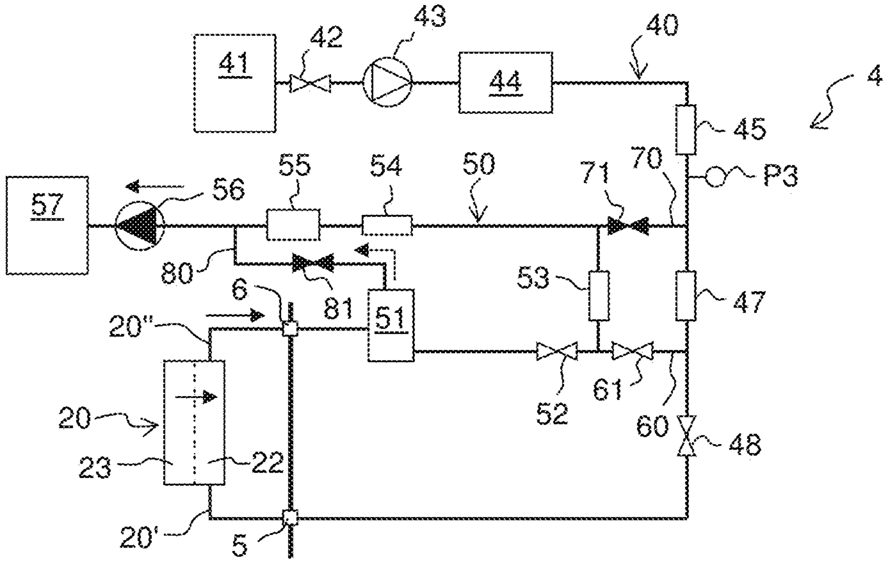

These principles will now be exemplified with reference to a conventional fluid supply unit 4 which is depicted in FIGS. 9A-9B. The fluid supply unit 4 defines a supply flow path 40 that extends from a dialysis fluid supply 41 to the outlet port 5 and includes a supply valve 42, a supply pump 43, a degassing device 44, a conductivity sensor 45, a pressure sensor P3, a flow sensor 47, and an outlet valve 48. The fluid supply system 4 also defines a drain flow path 50 that extends from the inlet port 6 to a drain 57 and includes a degassing device 51, an inlet valve 52, a flow sensor 53, a conductivity sensor 54, a blood detector 55, and a drain pump 56. A gas evacuation line 80 connects the degassing chamber 51 to the drain flow path 50 upstream of the drain pump 56 and includes an evacuation valve 81. In the illustrated example, fluid communication may be established between the first and second flow paths 40, 50, via either of a first and a second bypass line 60, 70 with a respective bypass valve 61, 71. The first bypass line 60 extends between an upstream end of flow sensor 53 and a downstream end of flow sensor 47, and the second bypass line 70 extends between a downstream end of flow sensor 53 and an upstream end of flow sensor 47. Although not shown in FIGS. 9A-9B, further sensors may be included in the inlet and outlet flow paths 40, 50, e.g. sensors included in a protective system of the machine 1.

The fluid supply unit 4 may be operated during blood treatment, by the control system 2 (FIG. 1), to generate a flow of fresh dialysis fluid through the outlet port 5 and a flow of spent dialysis fluid through the inlet port 6, as indicated by solid arrows in FIG. 9A. In the illustrated example, valves 42, 48 are open, supply 43 pump is active, bypass valves 61, 71 are closed, valve 52 is open and drain pump 56 is active. Further, evacuation valve 81 is opened, at least intermittently, to allow gases to be drawn from degassing device 51 along gas evacuation line 80 by drain pump 56, as indicated by a dashed arrow.

Figure 8:
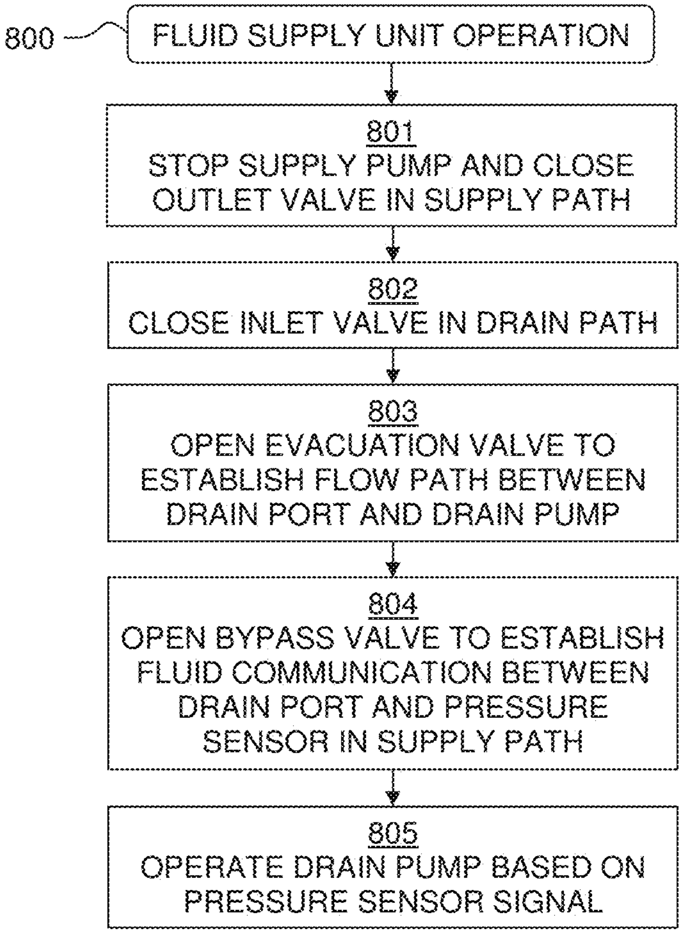
FIG. 8 is a flow chart of a method of operating a fluid supply unit of a dialysis machine in accordance with an embodiment.

FIG. 8 illustrates a method 800 of operating the fluid supply unit 4 for achieving the above-mentioned filtration during the draining phase. The control system 2 may execute the method 800 by generating suitable control signals for the valves and the pumps in the fluid supply unit 4. The resulting configuration of the fluid supply unit 4 is shown in FIG. 9B. In step 801, supply pump 43 is stopped and outlet valve 48 is closed. In the example of FIG. 9B, supply valve 42 may also be closed. In step 802, inlet valve 52 is closed. In step 803, evacuation valve 81 is opened to establish a flow path between drain port 6 and drain pump 56. In step 804, bypass valve 71 is opened to establish fluid communication between drain flow path 50 and the pressure sensor P3 in the supply flow path 40. In step 805, drain pump 56 is started to thereby draw residual fluid from dialyzer 20 into inlet port 6, via degassing device 51, evacuation line 81, and drain pump 56 into drain 57, as indicated by solid arrows in FIG. 9B. Thus, this unconventional use of the gas evacuation line 80 makes it possible to avoid exposing the sensors 53-55 in the drain flow path 50 to residual fluid. Further, by opening the bypass valve 71, the pressure sensor P3 will be responsive to pressure changes in the second chamber 22 of the dialyzer 20. Thus, in step 805, the drain pump 56 and thus the filtration may be controlled based on the output signal of the pressure sensor P3.

The method 800 may be implemented in any fluid supply unit 4 that defines a supply flow path (cf 40) and a drain flow path (cf 50) comprising a set of sensors (cf.

53-55), wherein step 803 generally involves opening a valve (cf. 81) located in a connecting line (cf. 80), which extends between a first location in the drain flow path intermediate an inlet port (cf 6) and an inlet valve (cf. 52) and a second location in the drain flow path intermediate a drain pump (cf. 56) and the set of sensors. Further, step 804 may generally involve opening a bypass valve (cf. 61, 71) in a bypass line (cf 60, 70), which extends between a third location in the drain flow path intermediate the inlet valve (cf. 52) and the second location, and a fourth location in the supply flow path intermediate a supply pump (cf. 43) and an outlet valve (cf 48), so as to establish fluid communication between the inlet port (cf. 6) and a pressure sensor (cf. P3) in the supply flow path.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the foregoing description is equally applicable to any machine or apparatus which is configured to perform extracorporeal blood treatment by use of a dialyzer or an equivalent filtration unit, including but not limited to hemodialysis, hemofiltration, hemodiafiltration, plasmapheresis, extracorporeal blood oxygenation, extracorporeal liver support/dialysis, ultrafiltration, etc.

Further, it is conceivable to arrange another existing branch line of the line set in one of the machine-controlled clamps. For example, conventional line sets may include a branch line for infusion of anticoagulant and/or a branch line for infusion of substitution fluid.

In a further variant, the branch line may be installed in any other machine-controlled clamp than the withdrawal and return clamps that may be present on the dialysis machine. For example, dialysis machines may comprise a venting clamp for engagement with a branch line ("venting line") connected to the drip chamber 25. It is also conceivable to omit steps 503-505 and perform step 508 by controlling the venting clamp in engagement with the venting line.

In a further variant, steps 503 and 505 are omitted, which means that the branch line is disconnected to be open to the atmosphere during steps 506-508.

Further, the above-mentioned toggling during step 508 may be achieved by instructing the operator to intermittently and manually pinch the branch line, e.g. by use of a manual clamp.

Still further, steps 509-511 may involve instructing the operator to manually pinch the return or withdrawal line 24', 24" and the branch line to create the desired negative pressure in the branch line at step 511.

The invention claimed is:

1. A control system for a blood treatment apparatus, the blood treatment apparatus comprising a fluid supply unit configured for installation of a dialyzer and a line set to thereby define a first flow circuit for conducting a fluid provided by the fluid supply unit through the dialyzer and back to the fluid supply unit, and to define a second flow circuit which is separated from the first flow circuit by a semi-permeable membrane of the dialyzer and comprises return and withdrawal lines for connection to a vascular system of a subject during a blood treatment session, said control system being configured to, subsequent to a termination of the blood treatment session:

generate an instruction for an operator to connect the second flow circuit to a first port of a container that holds a human-compatible fluid;

operate the blood treatment apparatus, with the second flow circuit connected to the first port, to push remaining blood in the second flow circuit into the vascular system of the subject through the return line while admitting the human-compatible fluid from the container into the second flow circuit;

generate an instruction for the operator to disconnect the return line from the vascular system of the subject and re-arrange the second flow circuit to define a closed loop by connecting the second flow circuit to a second port of the container so that the container is included in the closed loop; and operate, in a draining phase with the closed loop including the second flow circuit connected to the second port, the blood treatment apparatus so as to first circulate residual liquid in the closed loop through the container and then to draw the residual liquid from the closed loop into the first flow circuit through the semi-permeable membrane of the dialyzer.

2. The control system of claim 1, wherein, in the closed loop, the withdrawal line is connected in fluid communication with the first port of the container and the return line is connected in fluid communication with the second port of the container.

3. The control system of claim 1, wherein, in the closed loop, terminating connectors on the withdrawal and return lines are connected, directly or indirectly, to the first and second ports, respectively, of the container.

4. The control system of claim 1, which is further configured to, in the draining phase, operate a clamp of the blood treatment apparatus to selectively open a branch line, which is included in the line set and is arranged in fluid communication with the second flow circuit, so as to ventilate the closed loop.

5. The control system of claim 4, which is configured to, during the draining phase, operate the clamp to keep the branch line open and only intermittently close the branch line.

6. The control system of claim 4, which is configured to, in the draining phase, operate the clamp to repeatedly close the branch line.

7. The control system of claim 4, which is configured to, when terminating the draining phase, operate the clamp to close the branch line, operate the blood treatment apparatus to generate a sub-atmospheric pressure in the closed branch line, and operate the clamp to open the branch line to release the sub-atmospheric pressure.

8. The control system of claim 4, wherein one of the return and withdrawal lines is arranged in the clamp during the blood treatment session, and wherein the control system is further configured to, before the draining phase, generate an instruction for the operator to remove said one of the return and withdrawal lines from the clamp and install the branch line in the clamp.

9. The control system of claim 4, wherein the branch line is branched from the withdrawal line.

10. The control system of claim 4, which is further configured to, before the draining phase, generate an instruction for the operator to disconnect the branch line from a sensor port of the blood treatment apparatus.

11. The control system of claim 4, wherein the return line is arranged in the clamp and the withdrawal line is arranged in a further clamp of the blood treatment apparatus during the blood treatment session, wherein the branch line is branched from the withdrawal line downstream of the further clamp, wherein the control system is further configured to, before the draining phase, generate an instruction for the operator to remove the return line from the clamp, install the branch line in the clamp, and generate an instruction for the operator to disconnect the branch line from a sensor port of the blood treatment apparatus, and wherein the control system is further configured to, before generating the instruction for the operator to disconnect the branch line, close the further clamp and operate the blood treatment apparatus to generate a sub-atmospheric pressure in the withdrawal line downstream of the further clamp and in the branch line.

12. The control system of claim 1, wherein the fluid supply unit defines a drain flow path which extends from an inlet port for connection with the first flow circuit to a drain pump, wherein the drain flow path comprises a set of sensors and an inlet valve intermediate the inlet port and the set of sensors, wherein the fluid supply unit further defines a supply flow path, which comprises an outlet valve and extends from a supply pump to an outlet port for connection with the first flow circuit, wherein said control system is further configured to, in the draining phase:

close the outlet and inlet valves;

open a valve located in a connecting line, which extends between a first location in the drain flow path intermediate the inlet port and the inlet valve and a second location in the drain flow path intermediate the drain pump and the set of sensors; and operate the drain pump to draw the residual liquid from the closed loop into the first flow circuit through the semi-permeable membrane of the dialyzer and from the first flow circuit into the drain flow path via the inlet port.

13. The control system of claim 12, wherein the connecting line extends from a degassing device in the drain flow path, and wherein the control system is further configured to, during the blood treatment session, open the valve in the connecting line to expel gases from the degassing device through the connecting line.

14. The control system of claim 12, which is further configured to, in the draining phase:

open a bypass valve in a bypass line, which extends between a third location in the drain flow path intermediate the inlet valve and the second location, and a fourth location in the supply flow path intermediate the supply pump and the outlet valve, so as to establish fluid communication between the inlet port and a pressure sensor in the supply flow path; and control the drain pump based on a pressure signal from the pressure sensor.

15. A blood treatment apparatus, comprising a fluid supply unit configured to supply a fluid to a first flow circuit, a pump operable to engage with a second flow circuit, and the control system of claim 1.

16. A control system for a blood treatment apparatus, the blood treatment apparatus comprising a fluid supply unit configured for installation of a dialyzer and a line set to thereby define a first flow circuit for conducting a fluid provided by the fluid supply unit through the dialyzer and back to the fluid supply unit, and to define a second flow circuit which is separated from the first flow circuit by a semi-permeable membrane of the dialyzer and comprises return and withdrawal lines for connection to a vascular system of a subject during a blood treatment session, said control system being configured to, subsequent to a termination of the blood treatment session:

generate an instruction for an operator to connect the withdrawal line to a port of a container that holds a human-compatible fluid;

operate the blood treatment apparatus, with the withdrawal line connected to the port, to push remaining blood in the second flow circuit into the vascular system of the subject through the return line while admitting the human-compatible fluid from the container into the withdrawal line;

generate an instruction for the operator to disconnect the return line from the vascular system of the subject and re-arrange the second flow circuit to define a closed loop by connecting the return and withdrawal lines to be in fluid communication with the port of the container; and operate, in a draining phase with the closed loop including the return and withdrawal lines in fluid communication with the port of the container via a three-way manifold coupling unit, wherein the three-way manifold coupling unit comprises a first terminal fluidly connected to a first terminal connector and a second terminal fluidly connected to a second terminal connector, the blood treatment apparatus so as to first circulate residual liquid in the closed loop through the container and then to draw the residual liquid from the closed loop into the first flow circuit through the semi-permeable membrane of the dialyzer.

17. The control system of claim 16, which is further configured to, in the draining phase, operate a clamp of the blood treatment apparatus to selectively open a branch line, which is included in the line set and is arranged in fluid communication with the second flow circuit, so as to ventilate the closed loop.

18. The control system of claim 17, which is configured to, during the draining phase, operate the clamp to keep the branch line open and only intermittently close the branch line.

19. The control system of claim 17, which is further configured to, in the draining phase, operate the clamp to repeatedly close the branch line.

20. The control system of claim 17, which is configured to, when terminating the draining phase, operate the clamp to close the branch line, operate the blood treatment apparatus to generate a sub-atmospheric pressure in the closed branch line, and operate the clamp to open the branch line to release the sub-atmospheric pressure.

21. The control system of claim 17, wherein one of the return and withdrawal lines is arranged in the clamp during the blood treatment session, and wherein the control system is further configured to, before the draining phase, generate an instruction for the operator to remove said one of the return and withdrawal lines from the clamp and install the branch line in the clamp.

22. The control system of claim 17, which is further configured to, before the draining phase, generate an instruction for the operator to disconnect the branch line from a sensor port of the blood treatment apparatus.

23. The control system of claim 17, wherein the return line is arranged so as to operate with the clamp and the withdrawal line is arranged so as to operate with a further clamp of the blood treatment apparatus during the blood treatment session, wherein the branch line is branched from the withdrawal line downstream of the further clamp, wherein the control system is further configured to, before the draining phase, generate an instruction for the operator to remove the return line from the clamp, install the branch line in the clamp, and generate an instruction for the operator to disconnect the branch line from a sensor port of the blood treatment apparatus, and wherein the control system is further configured to, before generating the instruction for the operator to disconnect the branch line, close the further clamp and operate the blood treatment apparatus to generate a sub-atmospheric pressure in the withdrawal line downstream of the further clamp and in the branch line.

24. The control system of claim 16, wherein the fluid supply unit defines a drain flow path which extends from an inlet port for connection with the first flow circuit to a drain pump, wherein the drain flow path comprises a set of sensors and an inlet valve intermediate the inlet port and the set of sensors, wherein the fluid supply unit further defines a supply flow path, which comprises an outlet valve and extends from a supply pump to an outlet port for connection with the first flow circuit, wherein said control system is further configured to, in the draining phase:

close the outlet and inlet valves;

open a valve located in a connecting line, which extends between a first location in the drain flow path intermediate the inlet port and the inlet valve and a second location in the drain flow path intermediate the drain pump and the set of sensors; and operate the drain pump to draw the residual liquid from the closed loop into the first flow circuit through the semi-permeable membrane of the dialyzer and from the first flow circuit into the drain flow path via the inlet port.

25. A method of operating a blood treatment apparatus that comprises a fluid supply unit and is configured for installation of a dialyzer and a line set to define a first flow circuit for conducting a fluid provided by the fluid supply unit through the dialyzer and back to the fluid supply unit, and to define a second flow circuit which is separated from the first flow circuit by a semi-permeable membrane of the dialyzer and comprises return and withdrawal lines for connection to a vascular system of a subject during a blood treatment session, said method comprising, subsequent to a rinseback procedure and while the withdrawal line is connected to a first port of a container and when the return line has been disconnected from the vascular system of the subject:

generating an instruction for re-arranging the second flow circuit to define a closed loop, wherein said re-arrangement comprises connecting the second flow circuit to a second port of the container so that the container is included in the closed loop; and operating, in a draining phase, the blood treatment apparatus so as to first circulate residual liquid in the closed loop through the container and then to draw the residual liquid from the closed loop into the first flow circuit through the semi-permeable membrane of the dialyzer.

26. A non-transitory, computer-readable medium storing instructions which, when executed by a processor of the blood treatment apparatus, cause the processor to perform the method of claim 25.

27. A method of operating a blood treatment apparatus that comprises a fluid supply unit and is configured for installation of a dialyzer and a line set to define a first flow circuit for conducting a fluid provided by the fluid supply unit through the dialyzer and back to the fluid supply unit, and to define a second flow circuit which is separated from the first flow circuit by a semi-permeable membrane of the dialyzer and comprises return and withdrawal lines for connection to a vascular system of a subject during a blood treatment session, said method comprising, subsequent to a rinseback procedure and while the withdrawal line is connected to a port of a container and when the return line has been disconnected from the vascular system of the subject:

generating an instruction for re-arranging the second flow circuit to define a closed loop, wherein said re-arrangement comprises connecting the return and withdrawal lines in fluid communication with the port of the container through a three-way manifold coupling unit, wherein the three-way manifold coupling unit comprises a first terminal fluidly connected to a first terminal connector and a second terminal fluidly connected to a second terminal connector; and operating, in a draining phase, the blood treatment apparatus so as to first circulate residual liquid in the closed loop through the container and then to draw the residual liquid from the closed loop into the first flow circuit through the semi-permeable membrane of the dialyzer.

28. A non-transitory, computer-readable medium storing instructions which, when executed by a processor of the blood treatment apparatus, cause the processor to perform the method of claim 27.

* * * * *